US012201737B2

(12) United States Patent
Nayak

(10) Patent No.: US 12,201,737 B2
(45) Date of Patent: Jan. 21, 2025

(54) SANITIZATION SYSTEMS AND METHODS WITH UVC LIGHTING

(71) Applicant: Goodrich Corporation, Charlotte, NC (US)

(72) Inventor: Pramoda Kumar Nayak, Bangalore (IN)

(73) Assignee: GOODRICH LIGHTING SYSTEMS, INC., Oldsmar, FL (US)

( * ) Notice: Subject to any disclaimer, the term of this patent is extended or adjusted under 35 U.S.C. 154(b) by 669 days.

(21) Appl. No.: 17/373,164

(22) Filed: Jul. 12, 2021

(65) Prior Publication Data

US 2022/0370656 A1 Nov. 24, 2022

(30) Foreign Application Priority Data

May 24, 2021 (IN) .............................. 202141023114

(51) Int. Cl.
| | |
|---|---|
| A61L 2/10 | (2006.01) |
| B64D 11/00 | (2006.01) |
| B64D 41/00 | (2006.01) |
| B64D 47/02 | (2006.01) |
| B64F 5/30 | (2017.01) |

(52) U.S. Cl.
CPC ............... *A61L 2/10* (2013.01); *B64D 11/00* (2013.01); *B64D 41/00* (2013.01); *B64D 47/02* (2013.01); *B64F 5/30* (2017.01); *A61L 2202/11* (2013.01); *A61L 2202/14* (2013.01); *A61L 2202/16* (2013.01); *A61L 2202/25* (2013.01); *B64D 2011/0038* (2013.01)

(58) Field of Classification Search
CPC .... A61L 2/10; A61L 2202/11; A61L 2202/14; A61L 2202/16; A61L 2202/25; B64F 5/30; B64D 11/00; B64D 41/00; B64D 2011/0038
See application file for complete search history.

(56) References Cited

U.S. PATENT DOCUMENTS 7,323,065 B2 1/2008 Fencl et al.
8,226,887 B2 * 7/2012 Harmon .................... A61L 2/10
250/493.1

(Continued)

FOREIGN PATENT DOCUMENTS

EP 3228546 10/2017

OTHER PUBLICATIONS

European Patent Office, European Search Report dated Oct. 6, 2022 in Application No. 22175205.8.

(Continued)

*Primary Examiner* — Sean M Luck
(74) *Attorney, Agent, or Firm* — SNELL & WILMER L.L.P.

(57) ABSTRACT

A sanitization system for an aircraft may comprise: a lighting system disposed in the aircraft cabin, the lighting system including a plurality of sanitization lights, the plurality of sanitization lights configured to emit UV-C radiation; an electrical port in electrical communication with the lighting system; an external power source disposed away from the aircraft; and an electrical cable coupled to the external power source, the electrical cable configured to removably couple to the electrical port to provide electrical power to the plurality of sanitization lights.

17 Claims, 4 Drawing Sheets

(56) References Cited

U.S. PATENT DOCUMENTS

| | | | |
|---|---|---|---|
| 8,936,944 B2* | 1/2015 | Peltz | C12M 41/48 |
| | | | 436/178 |
| 9,517,280 B2* | 12/2016 | Lynn | A61L 2/10 |
| 9,550,006 B2 | 1/2017 | Boodaghians et al. | |
| 10,301,806 B2* | 5/2019 | Childress | A61L 2/10 |
| 10,307,504 B2 | 6/2019 | Munn | |
| 10,407,887 B2 | 9/2019 | Jensen | |
| 10,702,618 B2* | 7/2020 | Callahan | A61L 2/24 |
| 10,918,749 B2 | 2/2021 | Hatti et al. | |
| 10,933,821 B2* | 3/2021 | Line | A61L 2/10 |
| 11,007,292 B1 | 5/2021 | Grenon et al. | |
| 2004/0056201 A1* | 3/2004 | Fink | A61L 2/202 |
| | | | 250/352 |
| 2005/0022844 A1* | 2/2005 | Field | E01H 1/042 |
| | | | 134/6 |
| 2007/0053188 A1 | 3/2007 | New et al. | |
| 2010/0028201 A1* | 2/2010 | Neister | A61L 2/10 |
| | | | 73/29.02 |
| 2012/0221192 A1* | 8/2012 | Seibt | G01N 21/6456 |
| | | | 296/24.3 |
| 2012/0313532 A1* | 12/2012 | Stibich | A61L 2/10 |
| | | | 362/277 |
| 2013/0111917 A1* | 5/2013 | Ho | F02C 3/13 |
| | | | 60/773 |
| 2014/0044590 A1* | 2/2014 | Trapani | A61L 2/10 |
| | | | 422/3 |
| 2015/0013063 A1 | 1/2015 | Boodaghians | |
| 2015/0086420 A1* | 3/2015 | Trapani | A61L 9/20 |
| | | | 422/24 |
| 2016/0000951 A1* | 1/2016 | Kreiner | A61L 2/0047 |
| | | | 250/492.1 |
| 2016/0250362 A1* | 9/2016 | Mackin | B64D 11/06 |
| | | | 244/118.5 |
| 2016/0375166 A1 | 12/2016 | Kreitenberg | |
| 2017/0035920 A1 | 2/2017 | Boodaghians et al. | |
| 2018/0064833 A1* | 3/2018 | Childress | B64D 11/02 |
| 2018/0214591 A1* | 8/2018 | Park | B64F 5/30 |
| 2018/0361002 A1* | 12/2018 | Mastrocola | B64D 11/00 |
| 2019/0076558 A1 | 3/2019 | Zhang-Miske et al. | |
| 2020/0164988 A1* | 5/2020 | Alvarez | B64F 5/30 |
| 2020/0331611 A1* | 10/2020 | Hack | A61L 2/10 |

OTHER PUBLICATIONS

European Patent Office, European Office Action dated Jun. 11, 2024, in Application No. 22175205.8.

* cited by examiner

SANITIZATION SYSTEMS AND METHODS WITH UVC LIGHTING

CROSS-REFERENCE TO RELATED APPLICATIONS

This application is a non-provisional of, and claims priority to, and the benefit of India Provisional Application No. 202141023114 with access code 3DB5, entitled "SANITIZATION SYSTEMS AND METHODS WITH UVC LIGHTING," filed on May 24, 2021, which is hereby incorporated by reference in its entirety.

FIELD

The present disclosure relates generally to sanitization systems and methods and, more particularly, to sanitization systems and methods using UVC wavelength light for aircrafts.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization system for an aircraft cabin of an aircraft is disclosed herein. The sanitization system may comprise: a lighting system disposed in the aircraft cabin, the lighting system including a plurality of sanitization lights, the plurality of sanitization lights configured to emit UV-C radiation; an electrical port in electrical communication with the lighting system; an external power source disposed away from the aircraft; and an electrical cable coupled to the external power source, the electrical cable configured to removably couple to the electrical port to provide electrical power to the plurality of sanitization lights.

In various embodiments, the sanitization system further comprises a ground service cart, the external power source disposed in the ground service cart. The sanitization system may further comprise a sensor configured to detect whether the aircraft cabin is empty. The sanitization system may further comprise a controller configured to be operably coupled to the plurality of sanitization lights. The controller may be configured to: receive, through the sensor, sensor data; determine from the sensor data whether the aircraft cabin should be empty; and command the plurality of sanitization lights to emit the UV-C radiation for a predetermined period of time. A first light in the plurality of sanitization lights may be disposed above a row of seats, and wherein a second light in the plurality of sanitization lights is disposed above a walkway in the aircraft cabin. The electrical cable may comprise a plug, the plug configured to be removably coupled to the electrical port.

A sanitization system for an aircraft is disclosed herein. The sanitization system may comprise: a power source disposed external to the aircraft; an electrical cable electrically coupled to the power source, the electrical cable including a plug, the plug configured to removably couple to an electrical port of the aircraft; and a controller operably coupled to the power source, the controller configured to: receive, via a sensor disposed on the aircraft, sensor data; determine from the sensor data that the aircraft should be empty; and command a plurality of lights disposed in a cabin of the aircraft to emit UV-C radiation for a predetermined period of time.

In various embodiments, the sanitization system may further comprise a ground service cart, the power source disposed in the ground service cart. The UV-C radiation may include an average wavelength between 200 and 280 nm. The plurality of lights may be disposed in the cabin of the aircraft. The plurality of lights may be electrically coupled to the power source through the electrical port. The sanitization system may further comprise the sensor disposed proximate the cabin of the aircraft, the sensor in communication with the controller. The sensor may be a motion detection sensor.

An aircraft is disclosed herein. The aircraft may comprise: a first electrical system comprising a first power source and a plurality of cabin lights, the first power source in electrical communication with the first power source; and a second electrical system comprising a plurality of sanitization lights and an electrical port, the plurality of sanitization lights configured to emit UV-C radiation in a cabin of the aircraft, the plurality of sanitization lights in electrical communication with the electrical port, the first electrical system being at least electrically isolated from the second electrical system.

In various embodiments, the second electrical system may not be coupled to a second power source while the aircraft is in flight. The electrical port may be configured to couple to a plug of an electrical cable, the electrical cable in electrical communication with an external power source. The external power source may be disposed on a ground service cart. The aircraft may further comprise a sensor disposed in the aircraft, the sensor configured to detect motion in the cabin of the aircraft. The aircraft may further comprise a controller, wherein the sensor is configured to communicate with the controller, the controller configured to determine whether the aircraft is empty in response to receiving sensor data from the sensor.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings

DETAILED DESCRIPTION

Figure 1A:
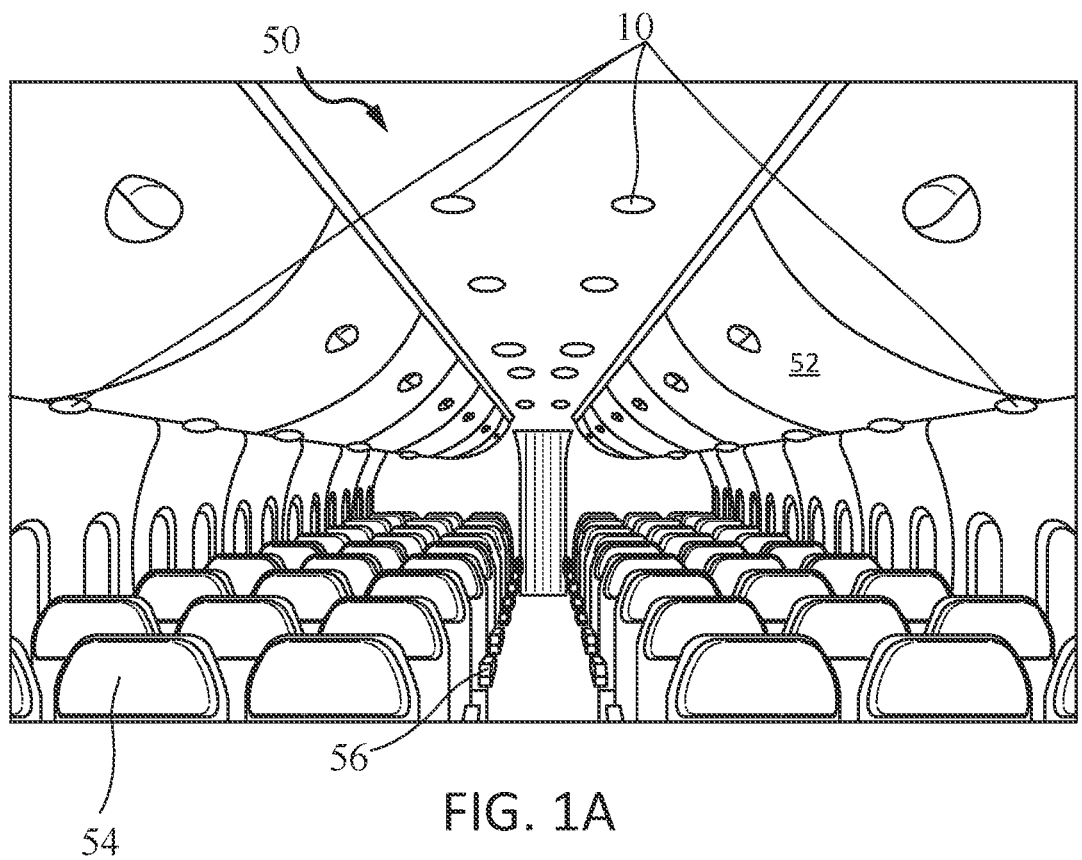
FIG. 1A illustrates a view of a cabin of an aircraft, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In various embodiments, ultraviolet C (UV-C) light (i.e., 200-280 nm wavelength light) has promise to work in unoccupied spaces such as an interior of a cabin or a cockpit of an aircraft for efficient disinfection of the interior. The UV-C light will kill certain viruses and bacteria on and around the interior surfaces. UV-C light may be more efficient, faster, and/or more cost-effective relative to typical sanitization systems for aircrafts. In various embodiments, in some respects, UV-C light may be harmful to humans when exposed for long durations. In various embodiments, a sanitization system for an aircraft may include UV-C lamps, or like disposed in a cabin, or cockpit, of an aircraft, the UV-C lamps being configured to operate when no passengers/crew are on the aircraft (i.e., after deboarding of an airplane). In this regard, the interior of the aircraft may be sanitized in an efficient manner without potential harmful effects for humans.

In various embodiments, a sanitization system as disclosed herein may comprise a first electrical system and a second electrical system independent from the first electrical system (e.g., at least electrically isolated from one another). In various embodiments, the first electrical system may be configured to operate during flight of the aircraft. For example, the first electrical system may include a power source disposed on the aircraft that is in electrical communication with aircraft lights and any other electrical components on the aircraft. The second electrical system may comprise an electrical port configured to couple to an external power source (e.g., a power source disposed on a ground service cart or the like). The electrical port may be in electrical communication with UVC lights disposed throughout the aircraft as described further herein. In this regard, the sanitization system may be configured to only operate when the aircraft is on-ground and furthermore may be configured to reduce the potential of the sanitization system being operated when passengers or crew remain on the aircraft. Thus, sanitizations systems as disclosed herein may avoid accidental switching on in flight and provide improved safety relative to typical aircraft sanitization systems, in accordance with various embodiments.

Figure 1B:
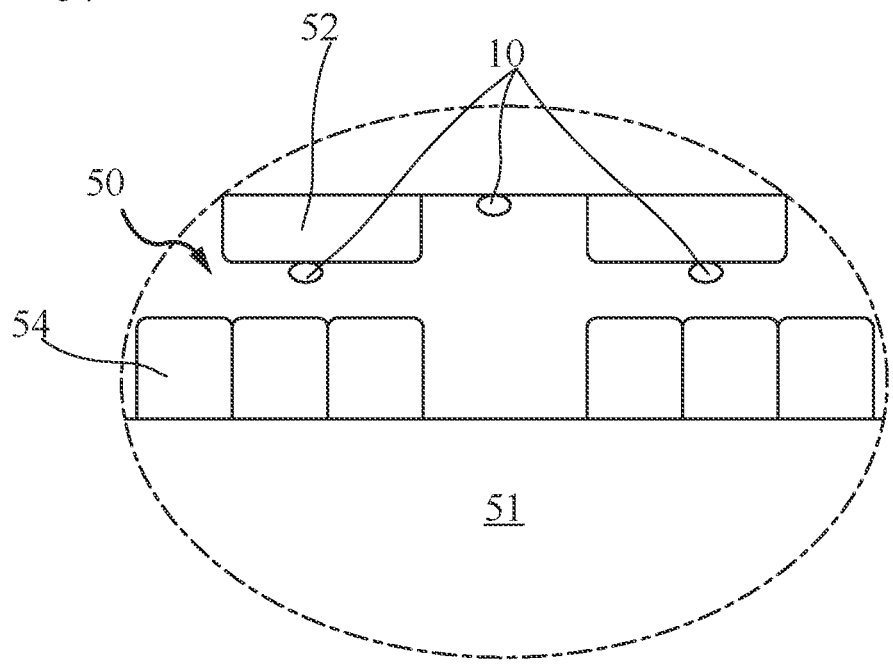
FIG. 1B illustrates a view of a cabin of an aircraft, in accordance with various embodiments.

With reference to FIGS. 1A and 1B, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers, handles 56, lavatory surfaces, and other structures/surfaces upon which active pathogens may temporarily reside. As will be discussed further below, in order to reduce the transmission/transfer of pathogens between passengers, one or more of the lighting systems 10 may emit disinfecting electromagnetic radiation output into the visible light in order to facilitate disinfection of the cabin 51 (e.g., between flights when the aircraft 50 is empty). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, a lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
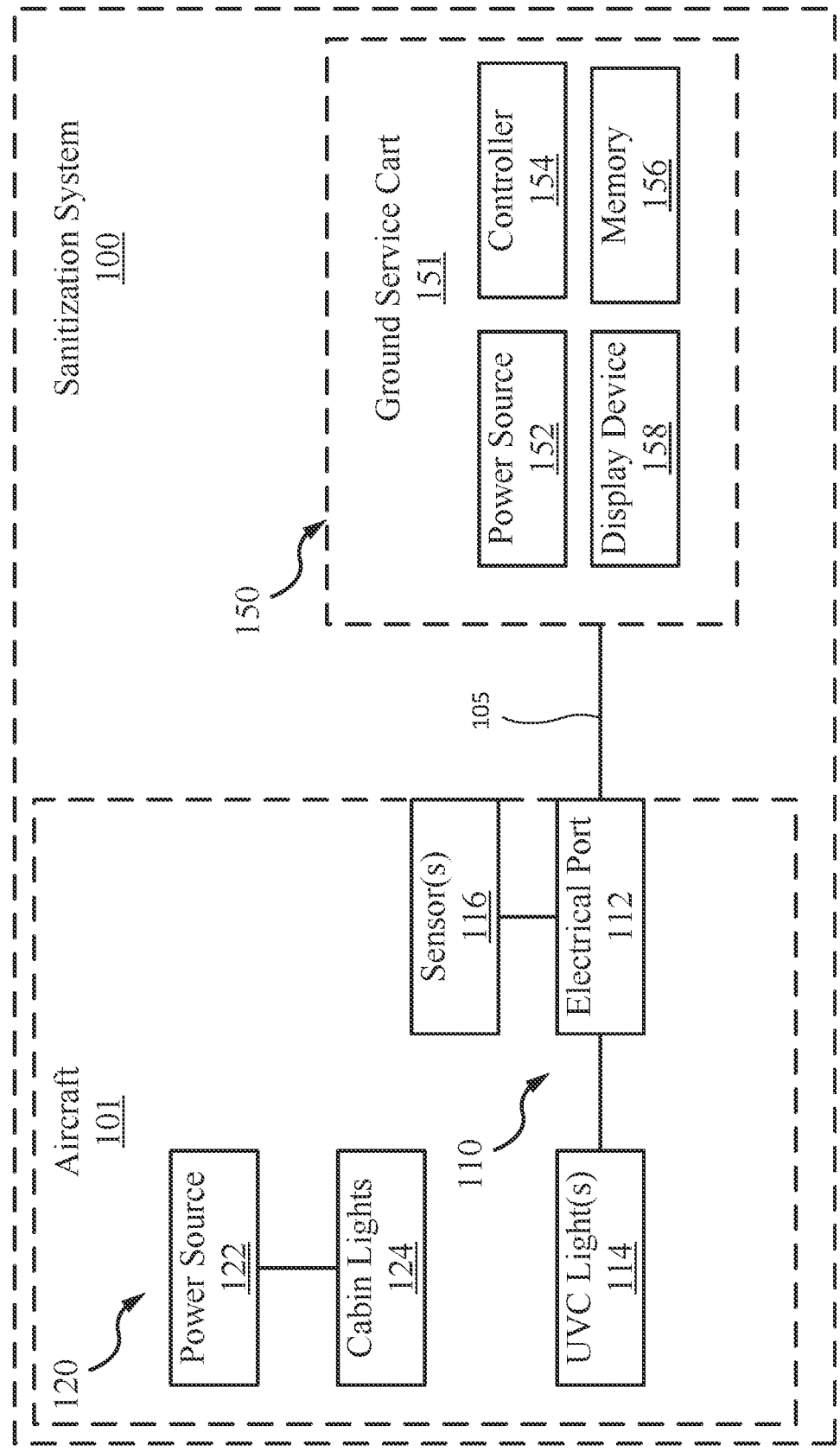
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises an aircraft 101 and a ground service cart 151. Although illustrated as a ground service cart 151, any external power source is within the scope of this disclosure (including a stationary external power source). For example, an external battery being coupled to an electrical port 112 of the aircraft 101 would be within the scope of this disclosure. In various embodiments, the aircraft 101 includes a first electrical system 110 and a second electrical system 120. In various embodiments, the second electrical system 120 is independent from the first electrical system 110 (e.g., at least electrically-isolated from one another). In various embodiments, the first electrical system 110 may comprise an electrical port 112, UV-C light(s) 114 and sensor(s) 116. In various embodiments, the second electrical system 120 includes a power source 122, cabin lights 124 and/or any other electrical component of the aircraft 101 configured to operate during flight of the aircraft 101. In various embodiments, the power source 122 is not in electrical communication with UV-C light(s) 114. In various embodiments, the UV-C light(s) 114 may be disposed throughout the cabin as illustrated in FIG. 1. For example, the UVC light(s) 114 may be disposed above rows of seats in a PSU, external to a PSU, or the like. The UV-C light(s) 114 may be disposed along the walkway. In various embodiments, the UV-C lights 114 may be disposed in the lavatory or the cockpit. The present disclosure is not limited in this regard. Thus, UV-C light(s) 114 may be disposed anywhere throughout the interior of the aircraft 101 where it may be desirable to have sanitization, in accordance with various embodiments.

In various embodiments, the sanitization system 100 comprises a control system 150. In various embodiments, the control system 150 includes a controller 154 and a memory 156 (e.g., a database or any appropriate data structure; hereafter "memory 156" also may be referred to as "database 156"). The controller 154 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 154 may utilize one or more processors of any appropriate type/configuration, may utilize any appropriate processing architecture, or both). In various embodiments, the controller 154 may further include any non-transitory memory known in the art. The memory 156 may store instructions usable by the logic device to perform operations. Any appropriate computer-readable type/configuration may be utilized as the memory 156, any appropriate data storage architecture may be utilized by the memory 156, or both.

The database 156 may be integral to the control system 150 or may be located remote from the control system 150. The controller 154 may communicate with the database 156 via any wired or wireless protocol (e.g., using any appropriate communication link). In that regard, the controller 154 may access data stored in the database 156. In various embodiments, the controller 154 may be integrated into computer systems onboard an aircraft. Furthermore, any number of conventional techniques for electronics configuration, signal processing and/or control, data processing and the like may be employed. Also, the processes, functions, and instructions may can include software routines in conjunction with processors, etc.

System program instructions and/or controller instructions may be loaded onto a non-transitory, tangible computer-readable medium having instructions stored thereon that, in response to execution by the processor, cause the controller 154 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 156 of the controller 154 may be configured to perform various operations. The schematic flow chart diagram of FIG. 3 includes a controller method 300 that the processor of the controller 154 may perform, in accordance with various embodiments. Generally, the controller 154 is operably (e.g., electrically or wirelessly through a network) coupled to the UV-C light(s) 114 as described further herein.

In various embodiments, the control system 150 further comprises a display device 158. In various embodiments, the display device 158 may be configured to provide inputs into the control system 150 for operation of the sanitization system 100. For example, the display device 158 may be used to set a duration for sanitization, set a wavelength of the UV-C light(s) 114, display a status of UV-C light(s) 114 (i.e., whether a UV-C light is operable or not), or the like. Although controller 154, memory 156 and display device 158 are illustrated as being components of the ground service cart 151, the present disclosure is not limited in this regard. For example, the controller 154, the memory 156, and the display device 158 may be components of the aircraft 101, in accordance with various embodiments.

In various embodiments, the control system 150 further comprises a power source 152. The power source 152 is disposed on the ground service cart 151. In various embodiments, the power source 152 is external to the aircraft 101. The power source 152 may be any power source, such as a battery, an electrical grid, or the like.

In various embodiments, the sanitization system 100 includes an electrical cable 105 coupled to the ground service cart 151. The electrical cable 105 is in electrical communication with the power source 152. In various embodiments, the electrical cable 105 is in electrical communication with the controller 154, the memory 156, and the display device 158. In various embodiments, the electrical cable 105 is configured to removably couple to the electrical port 112 via a plug, or the like. In this regard, in response to coupling the electrical cable 105 of the ground service cart 151 to the electrical port 112, the power source 152 becomes in electrical communication with the UV-C light(s) 114 of the first electrical system 110 of the sanitization system 100.

In various embodiments, sensor(s) 116 disposed on aircraft 101 may be utilized to reduce the potential of the sanitization system 100 being operated with personnel being within the aircraft cabin (e.g., cabin 51 from FIG. 1). For example, sensor(s) 116 may comprise motion detection sensors, such as passive infrared sensors, microwave motion sensors, dual tech motion sensors, or the like. In various embodiments, the sensor(s) 116 may be configured to determine whether an aircraft engine is off (i.e., an existing sensor of an aircraft engine may be electrically coupled to the ground service cart 151 and data from the sensor 116 may be utilized to verify the engine is off). In this regard, the sanitization system 100 may attempt to verify the aircraft 101 is empty, in accordance with various embodiments.

In various embodiments, the control system 150 is in operable communication with each UV-C light of the UVC light(s) 114 and sensor(s) 116. In various embodiments, each UV-C light in the UV-C light(s) 114 may comprise excimer lamp(s), light emitting diodes (LEDs), or the like. Each UV-C light 114 disclosed herein is configured to emit UV-C radiation. "UV-C" radiation, as disclosed herein, refers to radiation with wavelengths between 200 and 280 nms. In various embodiments, UV-C radiation may be safe for human exposure/consumption up to a certain dosage levels. However, extensive sanitization dosage levels post-flight may not be safe for human consumption. In this regard, the sanitization system 100 disclosed herein may provide various protections to reduce the potential for human consumption of output from UV-C light(s) 114, such as by utilizing sensor(s) 116 and/or by having the power source 152 of the sanitization system 100 being disposed external to the aircraft 101.

Figure 3:
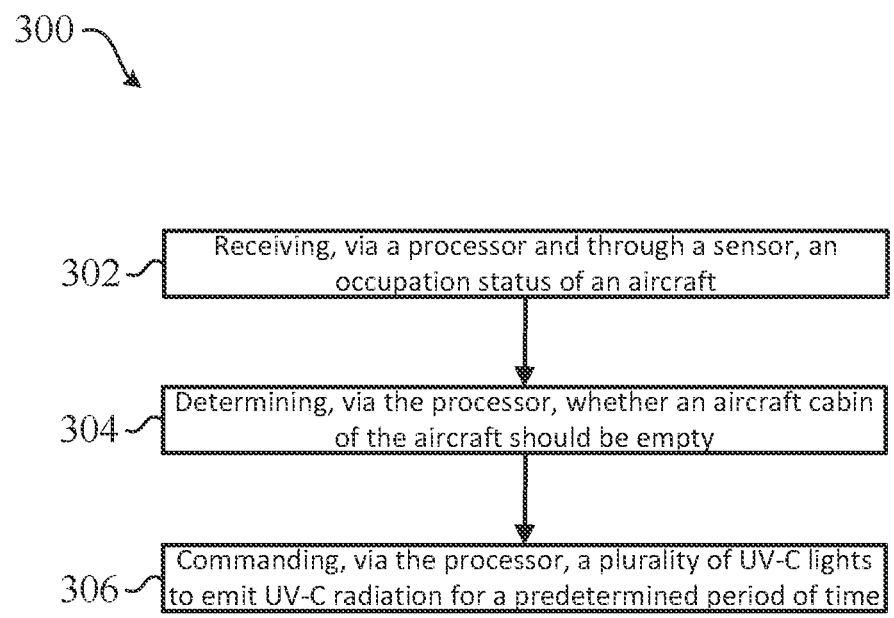
FIG. 3 is process performed by a control system for a sanitization system, in accordance with various embodiments.

Referring now to FIG. 3, a flow chart for a method 300 of operation for control system 150 from FIG. 2 is illustrated, in accordance with various embodiments. In various embodiments, the method 300 comprises receiving, via a processor (e.g., controller 154 from FIG. 2) and through a sensor (e.g., sensor(s) 116 from FIG. 2), an occupation status of an aircraft (step 302). In various embodiments, an occupation status may be empty or occupied. In various embodiments, the sensor may be configured to detect motion, determine whether an aircraft engine is off, or the like.

In various embodiments, the method 300 further comprises determining, via the processor, whether an aircraft cabin (e.g., cabin 51 from FIG. 1) should be empty (e.g., based upon identification of a condition that has been associated with an "empty" occupation status) (step 304). In this regard, the processor may receive the sensor data from step 302 and utilize the sensor data to determine whether the cabin should be empty based upon this sensor data. For example, for a motion sensor, if no motion is detected, the processor may associate this with the cabin being empty and if motion is detected, the processor may associate this with the cabin being occupied.

In various embodiments, the method 300 further comprises commanding, via the processor, a plurality of UV-C lights (e.g., UV-C lights 114 from FIG. 2) of lighting system 10 from FIGS. 1A-B) to emit UV-C radiation for a predetermined period of time (step 306). In various embodiments, the predetermined period of time may be determined based on an amount of time to sanitize a cabin (e.g., cabin 51 from FIG. 1). In various embodiments the period of time may be between 5 and 20 minutes, or approximately 10 minutes.

Figure 4:
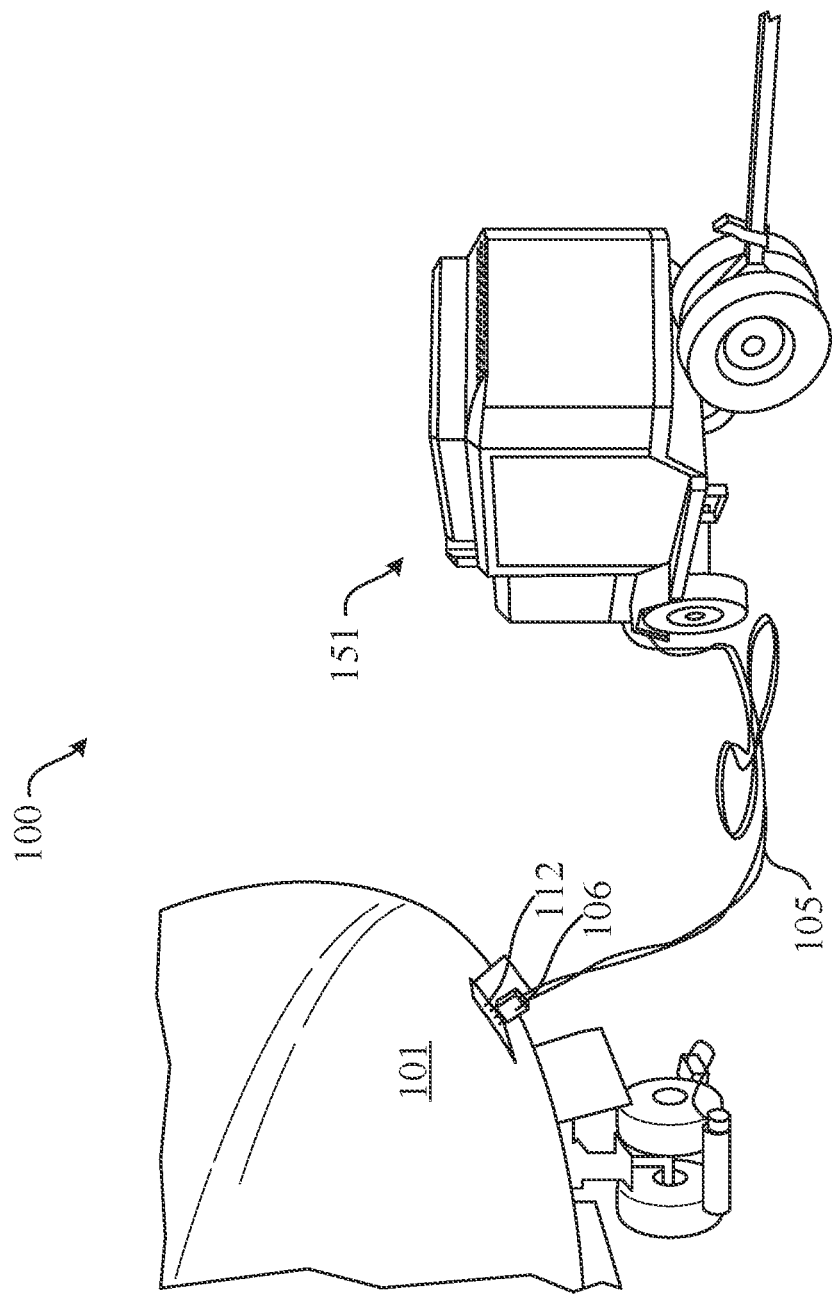
FIG. 4 illustrates a perspective view of a sanitization system in use, in accordance with various embodiments.

Referring now to FIG. 4, a perspective view of a ground service cart 151 in use in a sanitization system 100 for an aircraft 101 is illustrated, in accordance with various embodiments. In various embodiments, the electrical cable 105 is removably coupled to the electrical port 112 prior to operation of the sanitization system 100 via a plug 106. In various embodiments, the plug 106 may be three-pronged, two pronged or the like. In various embodiments, the electrical port 112 may comprise a ground fault circuit interrupter (GFCI) receptacle, or any other electrical receptacle.

In various embodiments, the sanitization system 100 disclosed herein may provide an efficient and cost effective way of cleaning an aircraft (e.g., aircraft 50 from FIG. 1A-B) relative to typical sanitization systems. In various embodiments, a sanitization system 100 disclosed herein may reduce the risk of infectious diseases spread due to certain virus or bacterial and provide better protection to passengers and crew members. In various embodiments, by having integral/built in UV-C lights 114 from FIG. 2 of a lighting system 10 from FIG. 1, a cabin (e.g., cabin 51 from FIGS. 1A-B) may be efficiently cleaned while the cabin is empty, maintaining safety of crew and passengers during sanitization.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization system, comprising:
an aircraft including:
   an interior and an exterior:
   an aircraft cabin disposed in the interior of the aircraft; and
   a first electrical system, comprising:
     a lighting system disposed in the aircraft cabin, the lighting system including a plurality of sanitization lights, the plurality of sanitization lights configured to emit UV-C radiation;
     a sensor configured to detect whether the aircraft cabin is empty;

an electrical port disposed on the exterior of the aircraft and in electrical communication with the lighting system;

a second electrical system comprising:
a first power source; and
a plurality of cabin lights, wherein the second electrical system is independent from the first electrical system; and a ground service cart configured to be disposed external from the aircraft during operation of the sanitization system, the ground surface cart including:
a housing;
an external power source disposed in the housing and away from the aircraft during operation of the sanitization system;
an electrical cable coupled to the external power source, the electrical cable configured to removably couple to the electrical port to exclusively provide electrical power to the plurality of sanitization lights; and
a controller configured to be operably coupled to the plurality of sanitization lights via the electrical cable, wherein in response to coupling the electrical cable to the electrical port the controller is configured to subsequently perform the following operations:
receive, through the sensor, sensor data;
determine from the sensor data whether the aircraft cabin should be empty; and
command the plurality of sanitization lights to emit the UV-C radiation for a predetermined period of time.

2. The sanitization system of claim 1, wherein a first light in the plurality of sanitization lights is disposed above a row of seats, and wherein a second light in the plurality of sanitization lights is disposed above a walkway in the aircraft cabin.

3. The sanitization system of claim 1, wherein the electrical cable comprises a plug, the plug configured to be removably coupled to the electrical port.

4. A sanitization system for an aircraft, the sanitization system comprising:
a ground service cart, including:
a power source disposed in the ground service cart and configured to be disposed external to the aircraft;
an electrical cable electrically coupled to the power source, the electrical cable including a plug, the plug configured to removably couple to an electrical port disposed on an exterior surface of the aircraft, wherein in response to coupling the plug to the electrical port disposed on the exterior surface of the aircraft, the power source is configured to electrically power a plurality of lights disposed within the aircraft; and
a controller operably coupled to the power source, the controller configured to be operably coupled to the plurality of lights via the electrical cable, wherein in response to coupling the plug to the electrical port disposed on the exterior surface of the aircraft, the controller configured to subsequently perform the following operations:
receive, via a sensor disposed on the aircraft, sensor data;
determine from the sensor data that the aircraft should be empty; and
command the plurality of lights disposed in a cabin of the aircraft to emit UV-C radiation for a predetermined period of time.

5. The sanitization system of claim 4, wherein the UV-C radiation includes an average wavelength between 200 and 280 nm.

6. The sanitization system of claim 4, further comprising the plurality of lights disposed in the cabin of the aircraft.

7. The sanitization system of claim 6, wherein the plurality of lights are electrically coupled to the power source through the electrical port.

8. The sanitization system of claim 6, further comprising the sensor disposed proximate the cabin of the aircraft, the sensor in communication with the controller.

9. The sanitization system of claim 8, wherein the sensor is a motion detection sensor.

10. An aircraft, comprising:
an aircraft cabin;
a first electrical system comprising a first power source and a plurality of cabin lights, the first power source in electrical communication with the first power source, each of the plurality of cabin lights coupled to and disposed within the aircraft cabin; and
a second electrical system comprising a plurality of sanitization lights and an electrical port, each of the plurality of sanitization lights coupled to and disposed within the aircraft cabin, each of the plurality of sanitization lights configured to emit UV-C radiation in a cabin of the aircraft, each of the plurality of sanitization lights in exclusive electrical communication with the electrical port, the first electrical system being electrically isolated from the second electrical system, the electrical port disposed on an exterior of the aircraft.

11. The aircraft of claim 10, wherein the second electrical system is not coupled to a second power source while the aircraft is in flight.

12. The aircraft of claim 10, wherein the electrical port is configured to couple to a plug of an electrical cable, the electrical cable in electrical communication with an external power source.

13. The aircraft of claim 12, wherein the external power source is disposed on a ground service cart.

14. The aircraft of claim 12, further comprising a sensor disposed in the aircraft, the sensor configured to detect motion in the cabin of the aircraft.

15. The aircraft of claim 14, further comprising a controller, wherein the sensor is configured to communicate with the controller, the controller configured to determine whether the aircraft is empty in response to receiving sensor data from the sensor.

16. The sanitization system of claim 1, further comprising the aircraft including an aircraft body and the aircraft cabin disposed within the aircraft body, wherein:
the first electrical system is disposed within the aircraft body;
the second electrical system is disposed within the aircraft body; and
the first power source is disposed within the aircraft body.

17. The sanitization system of claim 16, wherein the ground service cart is disposed external to the aircraft body during operation of the sanitization system.

* * * * *